(12) United States Patent
Obradovic (10) Patent No.: US 10,570,076 B2
(45) Date of Patent: Feb. 25, 2020

(54) METHOD FOR THE CONTINUOUS MANUFACTURE OF BISPHENOL A

(71) Applicant: SABIC GLOBAL TECHNOLOGIES B.V., Bergen op Zoom (NL)

(72) Inventor: Branislav Obradovic, Bergen op Zoom (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/304,315

(22) PCT Filed: Jul. 20, 2017

(86) PCT No.: PCT/IB2017/054405
§ 371 (c)(1),
(2) Date: Nov. 26, 2018

(87) PCT Pub. No.: WO2018/065834
PCT Pub. Date: Apr. 12, 2018

(65) Prior Publication Data
US 2019/0135719 A1    May 9, 2019

(30) Foreign Application Priority Data

Jul. 22, 2016    (EP) ..................................... 16180767

(51) Int. Cl.
*C07C 37/84*    (2006.01)
*C07C 37/20*    (2006.01)

(52) U.S. Cl.
CPC .............. *C07C 37/84* (2013.01); *C07C 37/20* (2013.01)

(58) Field of Classification Search
CPC ................................ C07C 37/84; C07C 37/20
See application file for complete search history.

(56) References Cited

U.S. PATENT DOCUMENTS

| | | |
|---|---|---|
| 4,766,553 A | 8/1988 | Kaya et al. |
| 6,033,635 A | 3/2000 | Gammill |
| 7,726,874 B2 | 6/2010 | Kirchberg |
| 2004/0030195 A1 | 2/2004 | Neumann et al. |
| 2005/0159631 A1 | 7/2005 | Koga et al. |
| 2009/0159257 A1 | 6/2009 | Marolt et al. |

FOREIGN PATENT DOCUMENTS

| | | |
|---|---|---|
| EP | 0330146 A1 | 8/1989 |
| JP | 2003126607 | 11/2004 |

OTHER PUBLICATIONS

International Search Report; International Application No. PCT/IB2017/054405; International Filing Date: Nov. 20 2017; dated Nov. 3, 2017; 5 pages.
Written Opinion; International Application No. PCT/IB2017/054405; International Filing Date: Nov. 20, 2017; dated Nov. 3, 2017; 5 pages.

*Primary Examiner* — Rosalynd A Keys
(74) *Attorney, Agent, or Firm* — Cantor Colburn LLP (57) ABSTRACT

In an embodiment, a method for the continuous manufacture of bisphenol A comprises reacting phenol and acetone in the presence of an acidic catalyst to form a product mixture comprising bisphenol A and phenol; directing the product mixture to a crystallization unit comprising a crystallization vessel and a heat exchanger for cooling the product mixture; and crystallizing bisphenol A-phenol adduct crystals from said product mixture in said crystallization unit to form a suspension of crystals; wherein a production rate of the bisphenol A through the heat exchanger is less than or equal to 18 kg bisphenol A per m of a heat exchanging surface per hour.

11 Claims, 5 Drawing Sheets

METHOD FOR THE CONTINUOUS MANUFACTURE OF BISPHENOL A

CROSS-REFERENCE TO RELATED APPLICATIONS

This application is a National Stage application of PCT/IB2017/054405, filed Jul. 20, 2017, which claims the benefit of European Application No. 16180767.2, filed Jul. 22, 2016, both of which are incorporated by reference in their entirety herein.

BACKGROUND

Bisphenol A is commercially produced by the condensation reaction of acetone and two equivalents of phenol in the presence of a catalyst such as an ion-exchange resin (IER). Bisphenol A is a high production volume compound with a world-wide estimated annual production of over 2 million tons. The demand for this compound is primarily due to its use as a monomer in the production of many high commodity materials such as epoxies and polycarbonates. In order to separate the formed bisphenol A from the product mixture, a crystallization step in a crystallization unit is often performed. The crystallization unit though is subject to frequent shut downs in order to reduce fouling buildup that often occurs.

An improved method for the production of bisphenol A that reduces or eliminates such shut-downs is therefore desirable.

US2004/0030195 discloses a process for preparing crystals of an adduct of a bisphenol and phenol.

BRIEF SUMMARY

Disclosed herein is a method of producing bisphenol A.

In an embodiment, a method for the continuous manufacture of bisphenol A comprises reacting phenol and acetone in the presence of an acidic catalyst to form a product mixture comprising bisphenol A and phenol; directing the product mixture to a crystallization unit comprising a crystallization vessel and a heat exchanger for cooling the product mixture; and crystallizing bisphenol A-phenol adduct crystals from said product mixture in said crystallization unit to form a suspension of crystals; wherein a production rate of the bisphenol A through the heat exchanger is less than or equal to 18 kg bisphenol A per $m^2$ of a heat exchanging surface per hour.

The above described and other features are exemplified by the following figures and detailed description.

BRIEF DESCRIPTION OF THE DRAWINGS

Refer now to the figures, which are exemplary, non-limiting embodiments, and wherein the like elements are numbered alike. Several of the figures are illustrative of the examples, which are not intended to limit devices made in accordance with the disclosure to the materials, conditions, or process parameters set forth herein.

DETAILED DESCRIPTION

Bisphenol A (BPA) production plants can comprise a crystallization unit comprising a crystallization vessel and a heat exchanger that can facilitate separation of the formed bisphenol A from both reactants and impurities. The amount of heat that can be removed in the heat exchanger is dependent upon the heat exchange surface area, the overall heat transfer coefficient, and the temperature differential. The term "temperature differential" as used herein refers to the difference in temperature between the cooled bisphenol A stream exiting the heat exchanger and the cooling inlet stream entering the heat exchanger, and when there are more than one heat exchangers operating in series the term refers to the difference in temperature between the cooled bisphenol A stream exiting the last heat exchanger in the series and the cooling inlet stream entering the first heat exchanger in the series; where it is understood that the bisphenol A stream and the cooling stream are not in physical contact with each other. When the plant production rates are increased, the temperature differential is increased in order to remove more heat, which can result in an increase in fouling. As the heat exchange surface area in the heat exchanger is constant, the easiest way to increase the amount of heat removed is to decrease the temperature of the entering cooling water, which results in an increase in the temperature differential. As the fouling increases, the circulation flow through the crystallization unit decreases and the overall heat transfer coefficient decreases. At a certain temperature differential, for example, 10 degrees Celsius (° C.), the crystallization process needs to be stopped so that one or both of the heat exchanger and the crystallization vessel can be cleaned by steaming and melting of the fouled crystals, respectively.

Stopping the production process to clean a heat exchanger can result in a loss in production of bisphenol A of over a ton and stopping the production process to clean the crystallization vessel can result in a loss in production of bisphenol A of over 80 tons as crystallization vessel cleaning generally takes a full day. Accordingly, stopping the crystallization process results in an expensive loss in bisphenol A production during the stopping time, especially in plants that experience high fouling. For example, plants running two crystallization lines each having two heat exchangers, can experience about 20 steam outs of various heat exchangers over the course of a day and a monthly cleaning of the crystallization vessels (i.e., 24 times per year).

It was surprisingly discovered that the increase in the temperature differential that results from an increase in fouling is directly dependent on the bisphenol A production rate. As used herein the term "production rate" refers to the amount of bisphenol A produced per heat exchange area with time, for example in kilograms of bisphenol A per meters squared per hour (kg bisphenol A/$m^2$ h). It was further surprisingly discovered that if the bisphenol A production plant operates at a production rate of less than or equal to 18 kg bisphenol A/$m^2$ h, then the process can be fouling free and the increasing temperature differential can be minimized or even eliminated. In other words, the method can be performed without stopping to clean a fouling build-up in either of the heat exchanger or of the crystallization vessel.

A method for the continuous manufacture of bisphenol A that results in little to no fouling was surprisingly discovered that comprises reacting phenol and acetone in the presence of an acidic catalyst to form a product mixture comprising bisphenol A and phenol; directing the product mixture to a crystallization unit comprising a crystallization vessel and a heat exchanger for cooling the product mixture; and crystallizing bisphenol A-phenol adduct crystals from the product mixture in the crystallization unit to form a suspension of crystals; wherein a production rate of the bisphenol A through the heat exchanger is less than or equal to 18 kg bisphenol A/m² h.

Figure 1:
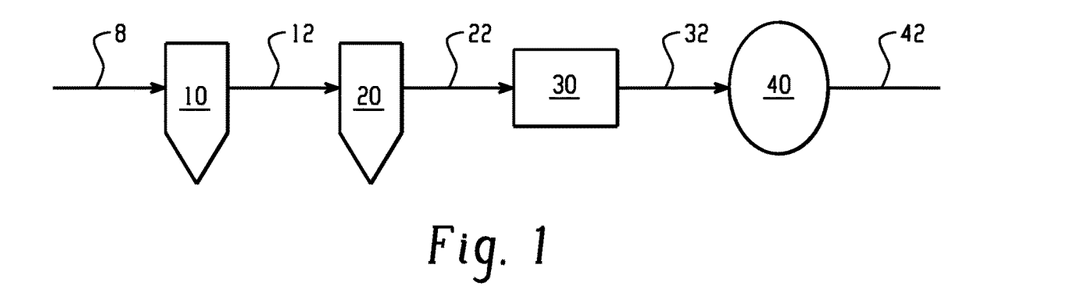
FIG. 1 is an illustration of an embodiment of a bisphenol A production facility.

FIG. 1 is an illustration of an embodiment of a bisphenol A production facility. FIG. 1 illustrates that reactor feed stream 8 can be directed to the bisphenol A reactor 10 to form bisphenol A stream 12. Reactor feed stream 8 can comprise phenol, acetone, and optionally a promoter. The reactor can be a fixed bed reactor comprising a catalyst. The catalyst can comprise an ion exchange resin (such as a tert-amine divinylbenzene/styrene ion exchange copolymer). The catalyst can comprise a strong acid catalyst (such as hydrochloric acid), a sulfonic resin and a sulfur containing promoter (such as a mercaptan promoter (such as methyl mercaptan, ethyl mercaptan, mercaptocarboxylic acid, 2,2-bis(methylthio)propane, and 3-mercaptopropionic acid)), as well as combinations comprising at least one of the foregoing. The phenol and acetone can be present in an amount of 5 to 15 moles of phenol per mole of acetone. Reactor feed stream 8 can comprise 75 to 95 weight percent (wt %) phenol and 3 to 7 wt % acetone. The phenol and acetone can be combined in a formulation tank located upstream of bisphenol A reactor 10. Bisphenol A stream 12 can be removed from bisphenol A reactor 10.

Bisphenol A stream 12 comprises the product mixture from the bisphenol A reaction. The product mixture can comprise one or more of 15 to 40 wt %, or 20 to 35 wt % of bisphenol A; 60 to 85 wt %, or 55 to 70 wt % of phenol; 5 to 15 wt % of byproduct; 0 to 5 wt %, or 0 to 3.5 wt % of water; and 0 to 8 wt %, or 0 to 1.5 wt % of acetone; all based on a total weight of the product mixture.

Bisphenol A stream 12 comprising the product mixture can be directed to crystallization unit 20 to form bisphenol A crystals comprising, for example, one or both of crystalline bisphenol A and an adduct of bisphenol A and phenol. It is noted that "adduct" as used herein refers to the physical association of bisphenol A and phenol (for example, one mole of bisphenol A and one mole of phenol can crystallize together to form a 1:1 molar ratio of bisphenol A/phenol adduct). The directing of the product mixture can comprise directing 300 to 1,000 tons of bisphenol A per day to the crystallization unit. The crystals can be separated by removing the solid portion from the crystallization unit 20 comprising the crystals, for example, via filtration, to form crystallized stream 22. The crystallization unit can comprise two or more crystallization units 20 operating in different lines. For example, the directing of the product mixture can comprise splitting the product mixture into two or more portions and directing each respective portion to a separate crystallization unit.

Figure 2:
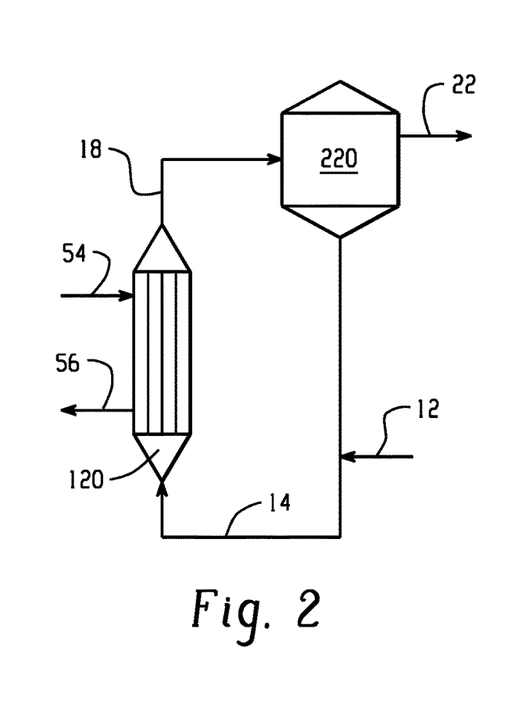
FIG. 2 is an illustration of an embodiment of a crystallization unit.

An embodiment of a crystallization unit is illustrated in FIG. 2 that illustrates that crystallization vessel 220 can be in fluid communication with heat exchanger 120. Here, cooling inlet stream 54 enters heat exchanger 120 and removes heat from bisphenol A stream 12 to form cooling outlet stream 56 that has a higher temperature than that of cooling inlet stream 54. Cooling inlet stream 54 can traverse through the heat exchanger 120 through a cooling jacket surrounding an inner region of the heat exchanger 120 comprising the bisphenol A stream 12. The heat exchanger can comprise a shell and tube heat exchanger.

Figure 3:
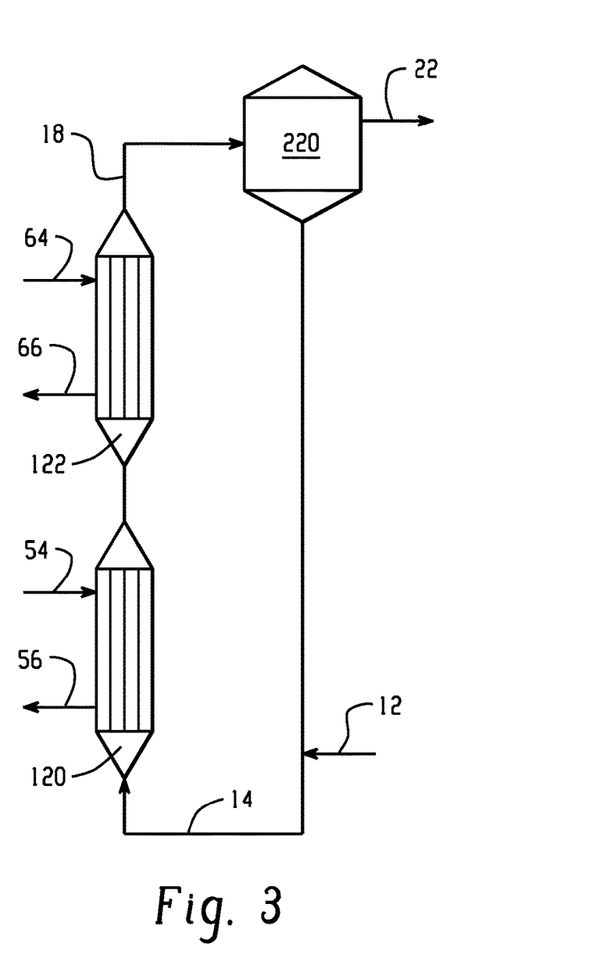
FIG. 3 is an illustration of an embodiment of a crystallization unit.

It is noted that while FIG. 2 illustrates only one heat exchanger 120, more than 1, or more than 2, or 2 to 10, or 2 to 8, or 2 to 4 inflow heat exchangers can be present. For example, FIG. 3 illustrates an embodiment where the crystallization unit comprises two heat exchangers 120 and 122, where heat exchanger 122 can also be referred to as downstream heat exchanger 122. A separate cooling stream is used in second heat exchanger 122, where second cooling inlet stream 64 enters heat exchanger 122 and removes heat from bisphenol A stream 12 to form second cooling outlet stream 66 that has a higher temperature than that of cooling inlet stream 64. FIG. 3 illustrates that crystallization vessel 220 can be in fluid communication with heat exchanger 120 and with second heat exchanger 122.

Bisphenol A stream 12 can be added to one or more of combined stream 14 as illustrated, to a heat exchanger, to cooled bisphenol A stream 18, and to crystallization vessel 220. Bisphenol A stream 12 can be added to one of combined stream 14 as illustrated or directly to a heat exchanger 120.

A temperature differential between cooled bisphenol A stream 18 exiting the heat exchanger (for example, a last heat exchanger in a series) and the cooling inlet stream 54 entering the heat exchanger (for example, a first heat exchanger in a series) can be less than or equal to 9° C., or less than or equal to 6° C.

Regardless of the specific configuration of the heat exchanger(s) in the crystallization unit(s), a heat exchanging surface area can be 150 to 2,000 meters squared (m²), or 150 to 300 m², or 150 to 700 m², or 300 to 700 m², or 700 to 2,000 m². The crystallization unit can comprise 2 to 10 heat exchangers each independently having a heat exchange surface area of 150 to 300 m².

Crystallized stream 22 can be directed to filter 30 to form filtered stream 32. Filter 30 can comprise a rotary vacuum filter. Filtered stream 32 can be directed to melting unit 40 to form melted stream 42. The melting unit 40 can melt the crystals, for example, by heating the crystals at a temperature greater than the crystallization temperature. An additional amount of phenol can be added to the filtered stream 32 to facilitate the melting of the crystals at a lower temperature. When the melted stream comprises sulfur, then a base (such as sodium hydroxide and potassium hydroxide) can be added to the melt to form a melt stream with a reduced sulfur content. The melted stream can be further purified to produce a product bisphenol A. The product bisphenol A can be solidified, for example, in a flaking unit, not shown in FIG. 1.

The production rate of the bisphenol A is less than or equal to 18 kg bisphenol A/m² h, or 2 to 18 kg bisphenol A/m² h. The production rate of the bisphenol A can be 2 to 10 kg bisphenol A/m² h, or 2 to 4 kg bisphenol A/m² h.

The following examples are provided to illustrate the present disclosure. The examples are merely illustrative and are not intended to limit devices made in accordance with the disclosure to the materials, conditions, or process parameters set forth therein.

EXAMPLES

Examples 1-5: Effect of the Production Rate on Crystallization Unit Fouling

Five experiments were performed to determine the effect of the production rate on the heat exchanger fouling of the crystallization unit by using different coolers having a different total tube surface area and by varying the flow rate of bisphenol A through the crystallization unit. The crystallization unit of Examples 1 and 2 comprised 4 separate heat exchangers each having a surface area of 285 m², the crystallization unit of Example 4 comprised 4 separate heat exchangers each having a surface area of 180.9 m², and the crystallization unit of Example 5 comprised 4 separate heat exchangers each having a surface area of 180 m². The flow of the bisphenol A in Example 3 was split into four lines. Three of the four lines were each directed to a crystallization unit having 2 heat exchangers each having a surface area of 180.9 m² and the fourth line was directed to a crystallization unit having two heat exchangers each having a surface area of 285 m². The results are shown in Table 1.

TABLE 1

|  | Example | | | | |
| --- | --- | --- | --- | --- | --- |
|  | 1 | 2 | 3 | 4 | 5 |
| Total tube surface area (m²) | 1,140 | 1,140 | 1,655 | 724 | 720 |
| Flow rate (tons per day) | 455 | 483 | 875 | 398 | 457 |
| Production rate (kg BPA/m²h) | 16.6 | 17.6 | 22 | 22.9 | 26.4 |
| Steam out required | No | No | Yes | Yes | Yes |

Table 1 shows that Examples 1 and 2 having production rates of less than 20 kg bisphenol A/m² h did not require a steam out during the crystallization process. In contrast, Examples 3-5, having production rates of greater than 20 kg bisphenol A/m² h, needed a steam out during the crystallization process.

Examples 6-9: Effect of Production Rate on the Temperature Differential

The effect of the production rate on the temperature differential and on steam out was determined by varying the flow rate of the bisphenol A through the crystallization unit of Example 5. The average flow rate for each of Examples 6-9 was 455 tons per day, 353 tons per day, 315 tons per day, and 300 tons per day, respectively, and a heat exchanger steam out was performed whenever the temperature differential was greater than 9.7° C. The resultant temperature differentials and flow rates with time are illustrated in FIGS. 4-7 for Examples 6-9, respectively.

Figure 4:
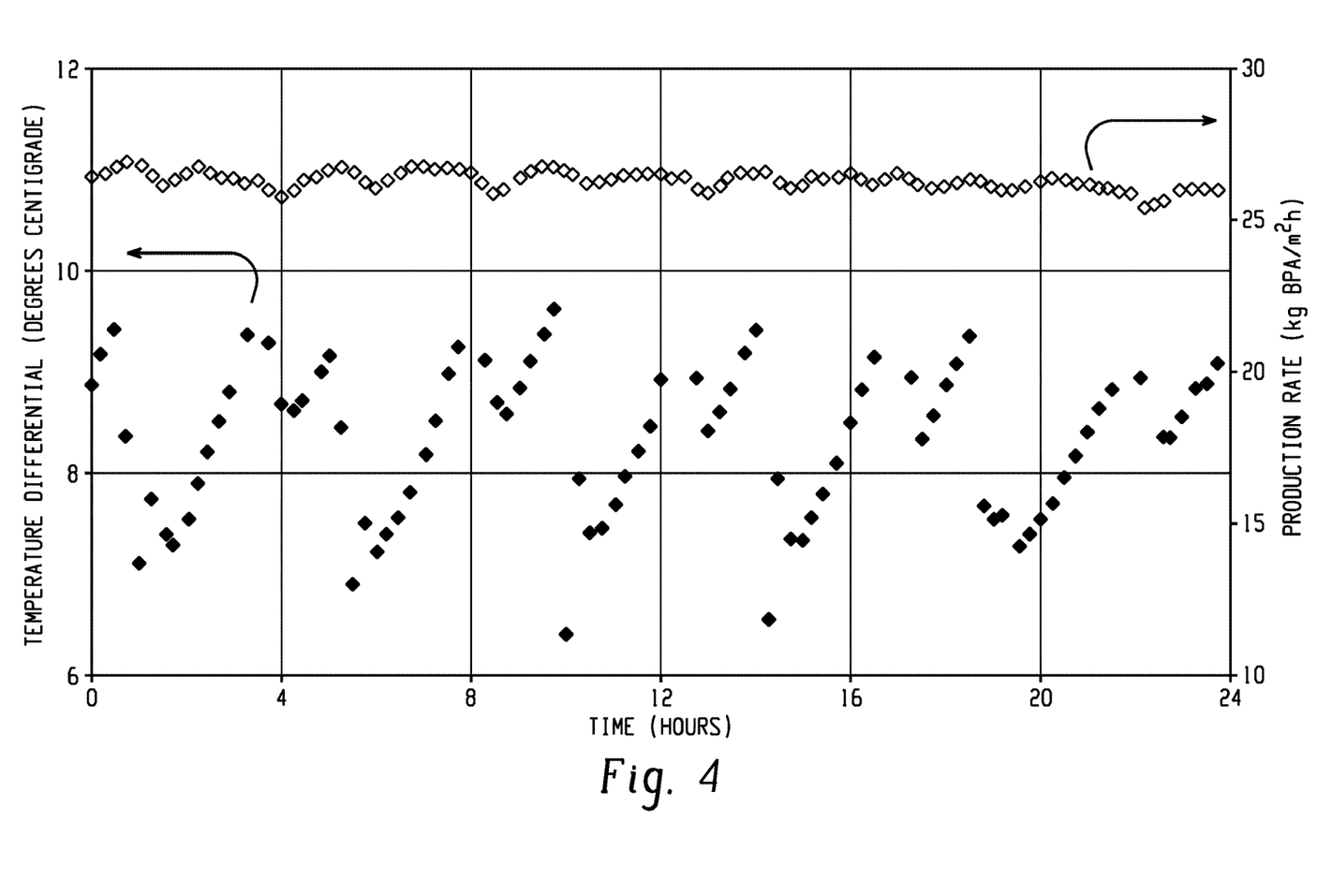
FIGS. 4-7 are graphical illustrations of the temperature differential and the production rate with time for Examples 6-9.
Figure 5:
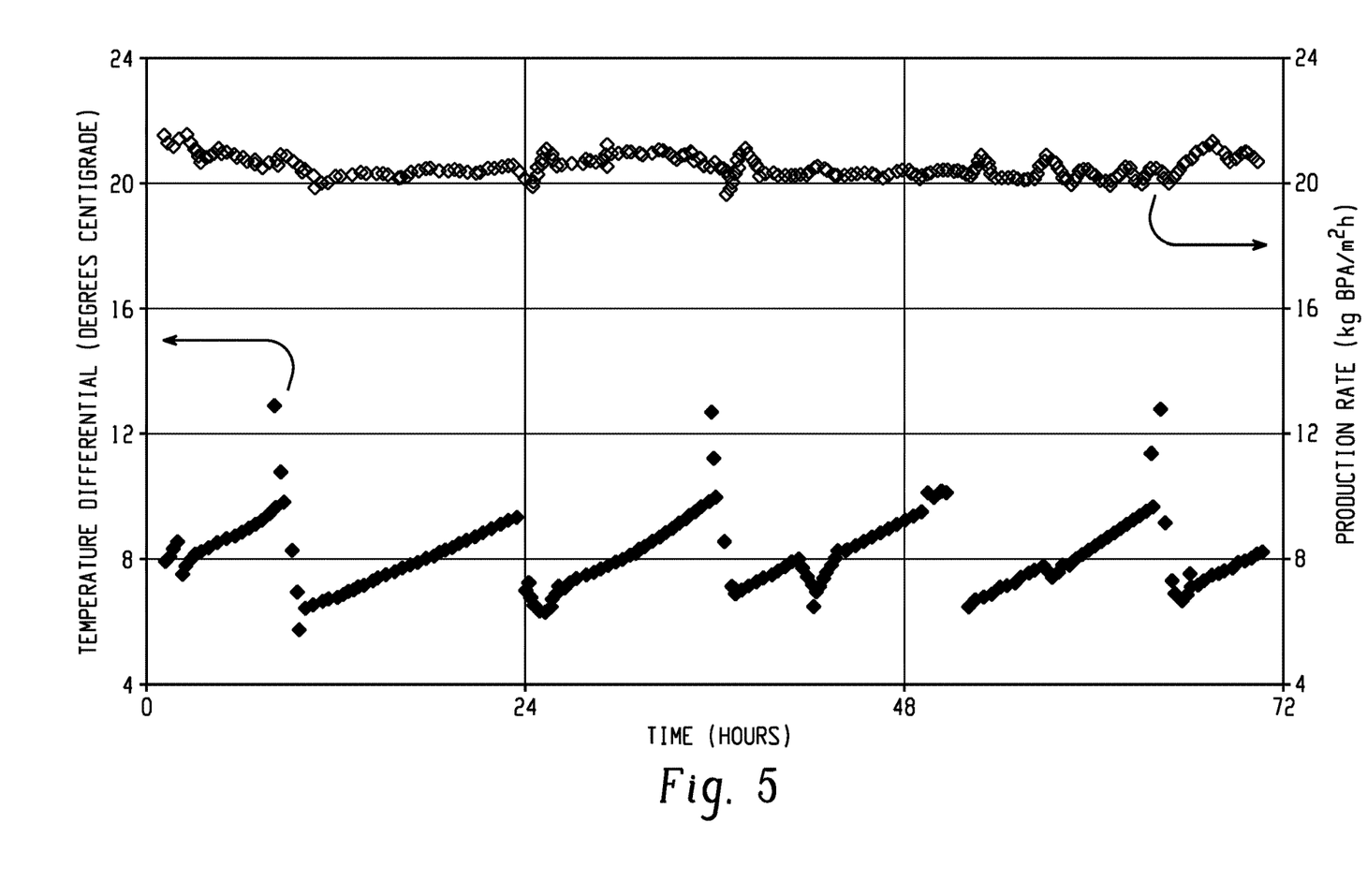
Figure 6:
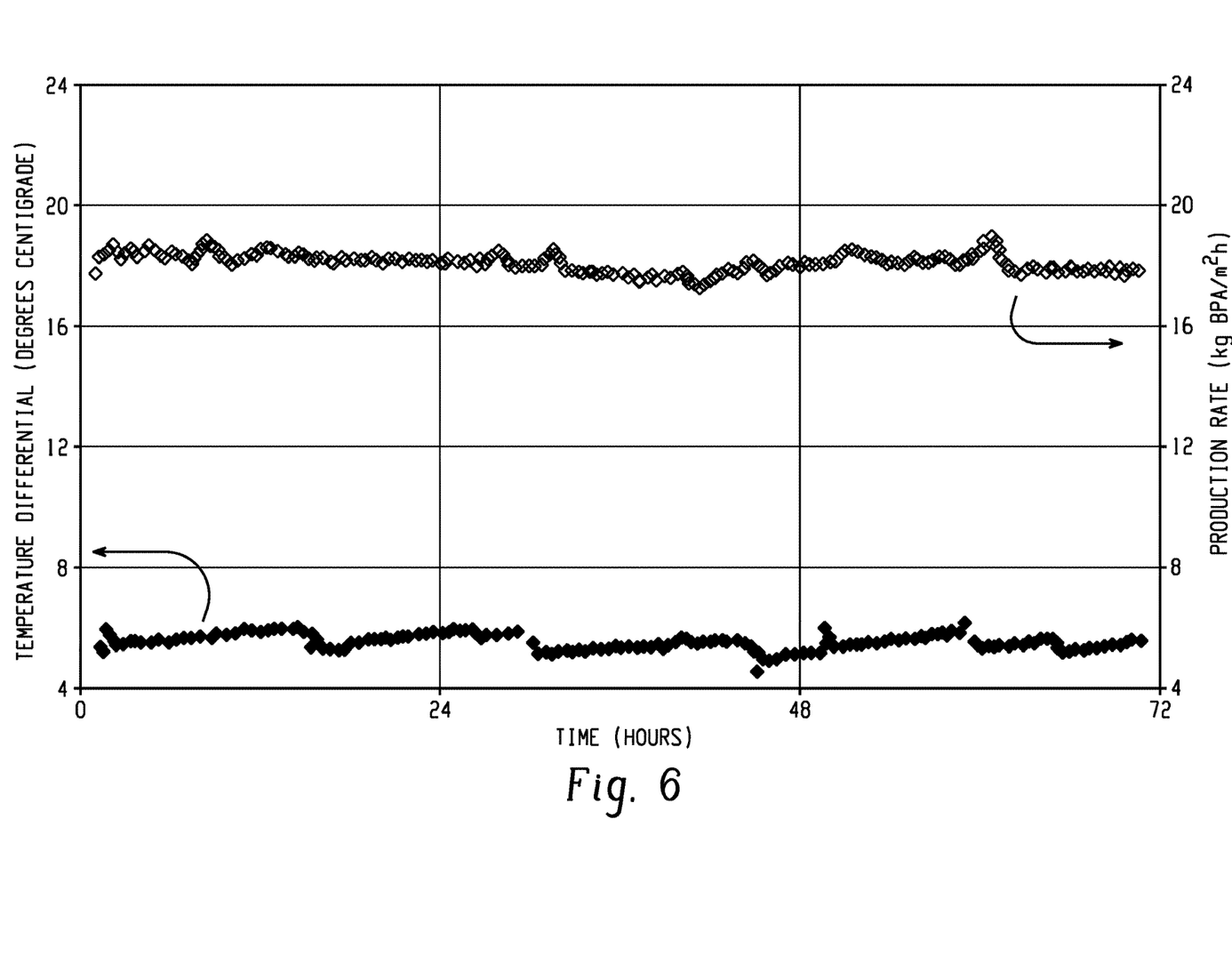
Figure 7:
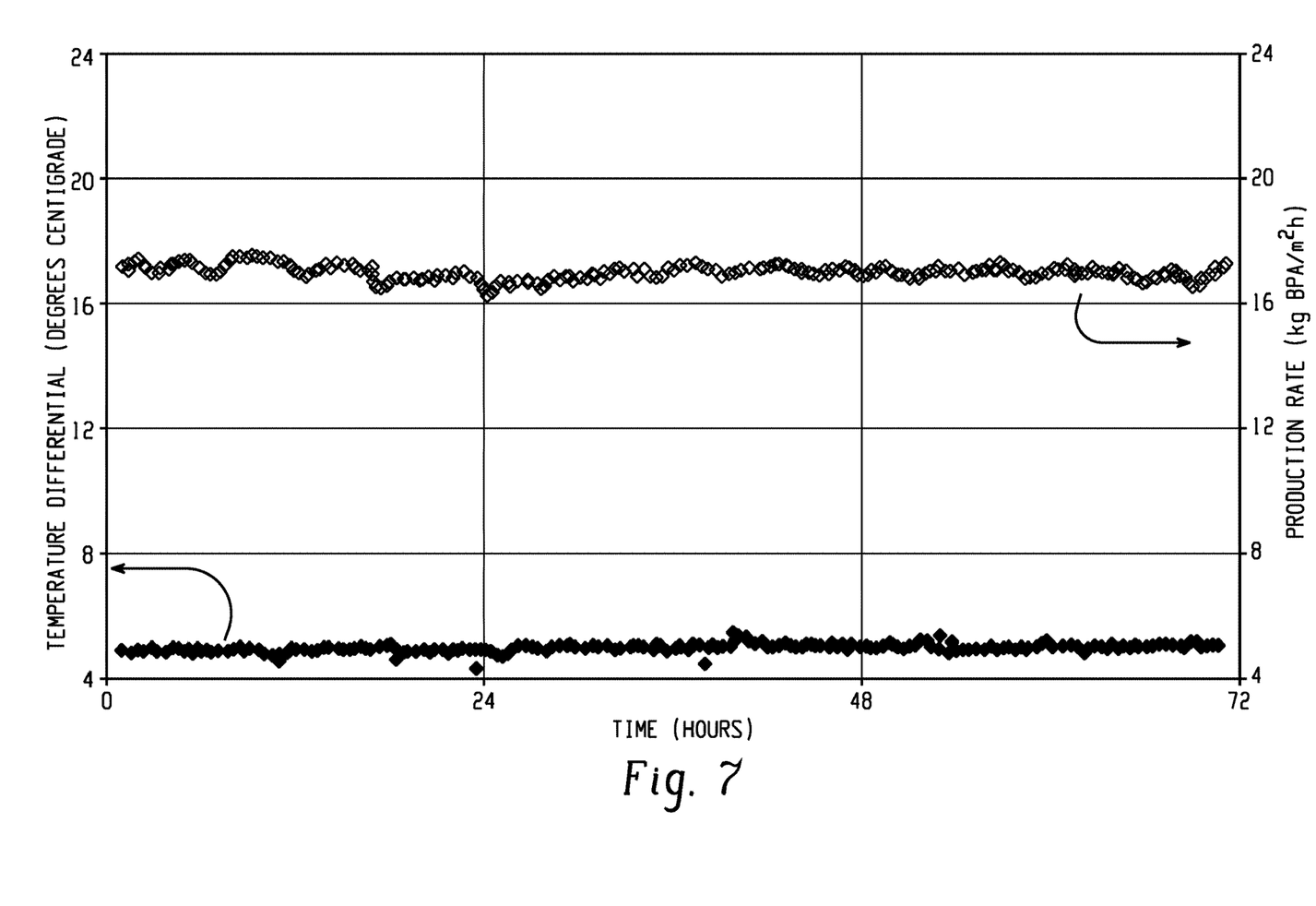

FIG. 4 shows that for a production rate of 26 kg Bisphenol A/m² h, a steam out of the heat exchanger occurred almost every four hours. FIG. 5 shows that reducing the production rate to 21 kg bisphenol A/m² h resulted in a reduction in the time between steam outs of the heat exchanger to about every 14 hours. FIG. 6 and FIG. 7 show that when the production rate is reduced to below 20 kg bisphenol A/m² h, the temperature differential does not reach 9° C. and steam outs were not needed.

Set forth below are non-limiting embodiments of the present method for producing bisphenol A.

Embodiment 1

A method for the continuous manufacture of bisphenol A comprising: reacting phenol and acetone in the presence of an acidic catalyst to form a product mixture comprising bisphenol A and phenol; directing the product mixture to a crystallization unit comprising a crystallization vessel and a heat exchanger for cooling the product mixture; and crystallizing the bisphenol A in said crystallization unit to form a crystallized stream comprising a suspension of crystals; wherein a production rate of the bisphenol A through the heat exchanger is less than or equal to 18 kg bisphenol A/m² h.

Embodiment 2

The method of Embodiment 1, wherein the production rate is 2 to 18 kg bisphenol A/m² h.

Embodiment 3

The method of any one or more of the preceding embodiments, wherein the crystallized bisphenol A comprises a crystallized bisphenol A, phenol adduct.

Embodiment 4

The method of any one or more of the preceding embodiments, wherein the product mixture comprises 20 to 35 wt % of bisphenol A, 55 to 70 wt % phenol, 0 to 3.5 wt % water, and 0 to 1.5 wt % acetone; all based on a total weight of the product mixture.

Embodiment 5

The method of any one or more of the preceding embodiments, wherein the product mixture comprises 0 to 1.5 wt % of acetone based on the total weight of the product mixture.

Embodiment 6

The method of any one or more of the preceding embodiments, wherein the crystallizing occurs in one crystallization unit.

Embodiment 7

The method of any one or more of Embodiments 1-5, wherein the directing comprises first splitting the product mixture into 2 or more portions and then directing each of the respective portions to a separate crystallization unit; and wherein the crystallizing occurs in two or more crystallization units.

Embodiment 8

The method of any one or more of the preceding embodiments, wherein a total heat exchanging surface area of the heat exchanger is 150 to 2,000 m².

Embodiment 9

The method of any one or more of the preceding embodiments, wherein the directing comprises directing 300 to 1,000 tons of bisphenol A per day.

Embodiment 10

The method of any one or more of the preceding embodiments, further comprising directing a cooling inlet stream into the heat exchanger; and wherein a temperature differential between the cooled bisphenol A stream and the cooling inlet stream is less than or equal to 9° C., preferably, less than or equal to 6° C.

Embodiment 11

The method of any one or more of the preceding embodiments, wherein the crystallization unit comprises at least two heat exchangers.

Embodiment 12

The method of Embodiment 11, wherein the crystallization unit comprises a first heat exchanger and a last heat exchanger; wherein a temperature differential between the cooled bisphenol A stream exiting the last heat exchanger and the cooling inlet stream entering the first heat exchanger is less than or equal to 9° C., preferably, less than or equal to 6° C.

Embodiment 13

The method of any one or more of the preceding embodiments, wherein the acidic catalyst comprises a sulfonated ion-exchange resin.

Embodiment 14

The method of any one or more of the preceding embodiments, further comprising directing the suspension of crystals to a solid liquid separation unit and separating the crystallized bisphenol A from the suspension.

Embodiment 15

The method of any one or more of the preceding embodiments, wherein the crystallization unit comprises 2 to 10 heat exchangers each independently having a heat exchange surface area of 150 to 300 m².

Embodiment 16

The method of any one or more of the preceding embodiments, wherein the crystallization unit comprises 2 to 8 heat exchangers each independently having a heat exchange surface area of 150 to 300 m².

Embodiment 17

The method of any one or more of the preceding embodiments, wherein a total heat exchanging surface area of the heat exchanger is 700 to 2,000 m².

Embodiment 18

The method of any one or more of the preceding embodiments, wherein the production rate is 2 to 10, or 2 to 4 kg bisphenol A/m² h.

In general, the disclosure can alternately comprise, consist of, or consist essentially of, any appropriate components herein disclosed. The disclosure can additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

The terms "a" and "an" do not denote a limitation of quantity, but rather denote the presence of at least one of the referenced item. The term "or" means "and/or" unless clearly indicated otherwise by context. Reference throughout the specification to "an embodiment", "another embodiment", "some embodiments", and so forth, means that a particular element (e.g., feature, structure, step, or characteristic) described in connection with the embodiment is included in at least one embodiment described herein, and may or may not be present in other embodiments. In addition, it is to be understood that the described elements may be combined in any suitable manner in the various embodiments. "Optional" or "optionally" means that the subsequently described event or circumstance may or may not occur, and that the description includes instances where the event occurs and instances where it does not. The suffix "(s)" as used herein is intended to include both the singular and the plural of the term that it modifies, thereby including one or more of that term (e.g., the colorant(s) includes one or more colorants). The term "combination" is inclusive of blends, mixtures, reaction products, and the like.

The endpoints of all ranges directed to the same component or property are inclusive of the endpoints, are independently combinable, and include all intermediate points. For example, ranges of "up to 25 wt %, or 5 to 20 wt %" is inclusive of the endpoints and all intermediate values of the ranges of "5 to 25 wt %," such as 10 to 23 wt %, etc.

In general, the compositions, methods, and articles can alternatively comprise, consist of, or consist essentially of, any ingredients, steps, or components herein disclosed. The compositions, methods, and articles can additionally, or alternatively, be formulated, conducted, or manufactured so as to be devoid, or substantially free, of any ingredients, steps, or components not necessary to the achievement of the function or objectives of the present claims.

Unless defined otherwise, technical and scientific terms used herein have the same meaning as is commonly understood by one of skill in the art to which this invention belongs.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While the disclosed subject matter is described herein in terms of some embodiments and representative examples, those skilled in the art will recognize that various modifications and improvements can be made to the disclosed subject matter without departing from the scope thereof. Additional features known in the art likewise can be incorporated. Moreover, although individual features of some embodiments of the disclosed subject matter can be discussed herein and not in other embodiments, it should be apparent that individual features of some embodiments can be combined with one or more features of another embodiment or features from a plurality of embodiments.

What is claimed is:

1. A method for the continuous manufacture of bisphenol A comprising:
reacting phenol and acetone in the presence of an acidic catalyst to form a product mixture comprising bisphenol A and phenol;
directing the product mixture to a crystallization unit comprising a crystallization vessel and a heat exchanger to form a cooled bisphenol A stream; and crystallizing bisphenol A-phenol adduct crystals from said product mixture in said crystallization unit to form a crystallized stream comprising a suspension of crystals;

wherein a production rate of the bisphenol A through the heat exchanger is less than or equal to 18 kg bisphenol A per $m^2$ of a heat exchanging surface per hour.

2. The method of claim 1, wherein the production rate is 2 to 18 kg bisphenol A/$m^2$ h.

3. The method of claim 1, wherein the product mixture comprises 20 to 35 wt % of bisphenol A,
55 to 70 wt % phenol,
0 to 3.5 wt % water, and
0 to 1.5 wt % acetone;
all based on a total weight of the product mixture.

4. The method of claim 1, wherein the product mixture comprises 0 to 1.5 wt % of acetone based on the total weight of the product mixture.

5. A method for the continuous manufacture of bisphenol A comprising:

crystallizing bisphenol A-phenol adduct crystals from said product mixture in said crystallization unit to form a crystallized stream comprising a suspension of crystals, crystallizing bisphenol A-phenol adduct crystals from said product mixture in said crystallization unit to form a crystallized stream comprising a suspension of crystals, wherein the crystallizing occurs in one crystallization unit;

wherein a production rate of the bisphenol A through the heat exchanger is less than or equal to 18 kg bisphenol A per $m^2$ of a heat exchanging surface per hour.

6. The method of claim 1, wherein a total heat exchanging surface area of the heat exchanger is 150 to 2,000 $m^2$.

7. The method of claim 1, wherein the directing comprises directing 300 to 1,000 tons of bisphenol A per day.

8. The method of claim 1, further comprising directing a cooling inlet stream into the heat exchanger; and wherein a temperature differential between the cooling inlet stream and the cooled bisphenol A stream is less than or equal to 9° C.

9. The method of claim 1, wherein the crystallization unit comprises at least two heat exchangers.

10. The method of claim 1, wherein the acidic catalyst comprises a sulfonated ion-exchange resin.

11. The method of claim 1, further comprising directing the suspension of crystals to a solid liquid separation unit; and separating the crystallized bisphenol A from the suspension.

* * * * *